United States Patent [19]

Toth et al.

[11] 4,355,281

[45] Oct. 19, 1982

[54] EDDY CURRENT SURFACE FLAW DETECTION EMPLOYING SIGNAL CORRELATION

[75] Inventors: James M. Toth, Lyndhurst; Tyler W. Judd, Chardon, both of Ohio

[73] Assignee: Republic Steel Corporation, Cleveland, Ohio

[21] Appl. No.: 66,387

[22] Filed: Aug. 14, 1979

Related U.S. Application Data

[63] Continuation-in-part of Ser. No. 915,547, Jun. 14, 1978, abandoned.

[51] Int. Cl.³ .................... G01N 27/72; G01R 33/12; G01N 27/82
[52] U.S. Cl. .................... 324/232; 324/237; 324/242
[58] Field of Search ............ 324/217, 225–227, 324/232, 236–238, 242, 243

[56] References Cited

U.S. PATENT DOCUMENTS

| | | | |
|---|---|---|---|
| 2,744,233 | 5/1956 | Paivinen | 324/227 |
| 3,263,809 | 8/1966 | Mandula et al. | 209/518 |
| 3,281,667 | 10/1966 | Dobbing | 324/241 |
| 3,340,466 | 9/1967 | Ono | 324/277 |
| 3,394,304 | 1/1968 | Green | 324/234 |
| 3,443,212 | 5/1969 | Renken | 324/240 |
| 3,497,799 | 2/1970 | Harmon | 324/237 |
| 3,636,441 | 10/1972 | Fujimura et al. | 324/64 |
| 3,675,118 | 7/1972 | Booth | 324/266 |
| 3,714,558 | 1/1973 | Swanepoel | 324/532.25 |
| 3,718,855 | 1/1973 | Rogel | 324/202 |
| 3,723,861 | 3/1973 | Samples | 324/237 |
| 3,739,262 | 6/1973 | Seeking | 324/234 |
| 3,866,116 | 2/1975 | Strauts et al. | |

OTHER PUBLICATIONS

Kennedy et al., "Signal Processing in Nondestructive Testing", Jour. of Testing & Eval., vol. 3, No. 1, pp. 26–45, Jan. 1975.

*Primary Examiner*—Gerard R. Strecker
*Assistant Examiner*—Walter E. Snow
*Attorney, Agent, or Firm*—Watts, Hoffmann, Fisher & Heinke Co.

[57] ABSTRACT

An eddy current flaw detection system for inspecting a workpiece for surface flaws is described. The system has a search unit for mounting a pair of eddy current search coils in close proximity to a workpiece at locations which are longitudinally spaced with respect to the workpiece. The system is disclosed in the environment of a workpiece support and transport mechanism which causes a workpiece to rotate and move axially with respect to the search unit.

Coil energizing and detection circuitry is provided having a pair of eddy current channels. Each channel energizes a connected one of the search coils to induce eddy currents within a workpiece at slightly different energization frequencies. Each channel has an output for producing signals indicating the presence and severity of detected flaws. The coil energization at different frequencies results in each coil responding to self induced eddy currents rather than currents induced by the other of the two coils.

Processing circuitry is provided having a pair of inputs each connected to a respective eddy current channel output. The processing circuitry algebraically multiplies concurrently received eddy current channel output signals to produce a resultant signal. The disclosed signal correlation circuitry will not process a signal from a single coil. Accordingly, the axial separation of the search coils establishes a minimum length of surface flaw which will be detected. The value of the resultant signal indicates the severity of the detected surface flaw.

6 Claims, 5 Drawing Figures

EDDY CURRENT SURFACE FLAW DETECTION EMPLOYING SIGNAL CORRELATION

CROSS REFERENCE TO RELATED APPLICATION

This application is a continuation-in-part of application Ser. No. 915,547 filed June 14, 1978, entitled "Method and Apparatus for Eddy Current Flaw Detecting", now abandoned.

BACKGROUND OF THE INVENTION

This invention relates to a method and apparatus for sensing the condition of a workpiece, and more particularly, to a method and apparatus for eddy current flaw inspection.

1. Field of the Invention

Eddy current flaw detection systems are now routinely used in many steel manufacturing operations. These systems are especially useful in detecting surface flaws which are difficult to locate with visual or other inspection techniques. These systems are used not only because of their reliability in locating flaws which are otherwise difficult to locate, but also because they give an indication of the depth or the severity of a detected flaw.

2. Background of the Invention

Farrow U.S. Pat. No. 2,434,203 is an early teaching of one type of eddy current flaw detection. With the Farrow system, separate energizing and detection coils encircle the workpiece. A workpiece standard corresponding to the workpiece is encircled by comparable energizing and detection coils.

The standard and workpiece detection coils are part of a Wheatstone bridge circuit. Variations in the current of the workpiece detection coil, caused by flaws in the workpiece, imbalance the Wheatstone bridge and produce output signals. Subsequent developments eliminated the Wheatstone bridge by simply comparing detector coil output signals to known reference signals or standards.

Sower U.S. Pat. No. 3,234,457 shows a detector coil having two balanced windings. That is a detector coil in which one-half of the windings are wound in one direction and the other half in the opposite direction so that, in the absence of a flaw, induced current in the windings are equal and opposite and there is no signal output. This permits, as Sower discloses and claims, movement of a detection coil relative to an excitation coil without producing spurious output signals. Harmon U.S. Pat. No. 2,914,726 eliminated, for some applications, the excitation coil using a single or a set of balanced coils for both eddy current induction and flaw detection.

With each of these described eddy current systems a magnetic field induces the flow of current in the test piece as the test piece and excitation source are moved relatively. These eddy currents flow around surface discontinuities causing variations in the eddy current flow which a sensing coil can detect. The variations cause output signals to be produced by the detection coil. The magnitude or value of such output signal is a function of the severity of the flaw and indicative of flaw depth.

A factor which limits the detector capabilities of eddy current detection is the signal-to-noise ratio. That is, the noise inherent in the system is of such magnitude that only those flaws which cause output signals of distinct and discernible value in excess of the background noise are detected. There is also the problem of being certain that a given output signal is caused by a surface flaw and not some harmless irregularity, such as scale on the surface of the workpiece.

Certain correlation techniques for improving signal-to-noise ratios have been known for many years. While these techniques have been known, their use has been limited by and large, if not exclusively, to such applications as LORAN or space communications. That is, they have been used in those applications where the signals are repetitive, at known time intervals, so that with electronic techniques the signals can be brought into time coordinated relationship and multiplied together. This multiplication amplifies the repetitive and desired signals and filters out the random and undesired noise.

While there was a suggestion for using either cross-correlation or auto correlation techniques in a reflective-type magnetic flaw inspection system, there was no teaching for how this proposal was to be brought to reality.

SUMMARY OF THE INVENTION

With the present invention, a plurality of output pulses are developed. These output pulses are fed to an analog multiplier processing circuit in a time coordinated manner. The processing enhances the value of distinct pulses indicative of flaws and filters out, or at least relatively reduces, background noise so that the signal-to-noise ratio of flaw indicating pulses to background noise is substantially increased.

In the preferred system, distinct pulses are time coordinated by taking signals at spaced locations along a single flaw. With this technique, flaws of a length less than a predetermined maximum acceptable length are ignored. Output correlated signals are only produced when there have been distinct signals from the same flaw, or in extremely unlikely condition of two flaws at locations spaced axially a distance corresponding to coil spacing, and this condition can be ignored.

The output pulses are generated in response to excitation of the workpiece at two slightly different energization frequencies. One excitation/detection coil resonates at a frequency slightly greater than the other. Each coil is energized at its own resonant frequency and responds to induced eddy currents which oscillate with that frequency. In this way the coils respond primarily to self induced signals and not to signals induced by the other coil.

This signal correlation technique permits, then, a new inspection method which both rejects signals that provide information with respect to flaws less than a preestablished minimum length and reduces the minimum flaw depth which can be detected.

In many steel products, such as bar stock, the formation techniques elongate the workpiece as its cross-sectional dimension is diminished. As a consequence, surface flaws tend to be elongated and, surface flaws which appear in bar stock and other products are elongated axially.

In the preferred arrangement, time coordinated signals of a single flaw are produced by providing a spaced pair of detection coils. Since the surface flaws extend axially, the spaced pair of probes or detection coils are positioned at axially-spaced locations along a workpiece path. A bar is then fed along that workpiece path and rotated as it moves axially so that each detection coil inspects a different spiral path along the surface of the workpiece. Ideally, the feed rates are such that the two spaced paths are substantially touching but not overlapping so that the entire workpiece surface is inspected in a minimum of time.

When the two coils produce concurrent output signals they represent output signals of a signal elongate flaw that has a length of sufficient dimension to be concurrently inspected by both of the coils. When these two outputs are multiplied together in the signal correlation circuitry, an output signal indicative of the nominal depth of the flaw is produced. This signal can then be compared against a reference signal in a known manner and used, also in known ways, to cause a marking device to mark the location of the detected flaw.

A relatively large percentage of current steel manufacturing is to fill specific customer needs. For example, a quantity of bar stock may be produced for use in making axles. To be acceptable the stock must meet specifications for the type and severity of surface flaws which are to be detected with eddy current devices of the types that have been described.

In this example, the axle manufacturer must use a bar stock of a diameter equal to the maximum axle diameter plus 2X, where X is the minimum flaw depth which can be detected. In other words, the axle manufacturer must select the bar stock of sufficient diameter to be certain that the machining operation will remove all undetected surface flaws.

With a device made in accordance with the present invention, very shallow flaws can be detected to minimize the waste both in the amount of steel which must be purchased and workpiece processing time required to make a given finished product. Accordingly, while eddy current flaw inspection has enjoyed wide acceptance and success, there is continuing need for improving the flaw inspection capabilities of such systems particularly their ability to detect and identify shallow flaws and the present invention sastisfies that need.

The objects of the invention are to provide a novel and improved eddy current flaw inspection apparatus and a method of inspecting workpieces.

THE DRAWINGS

Figure 4:
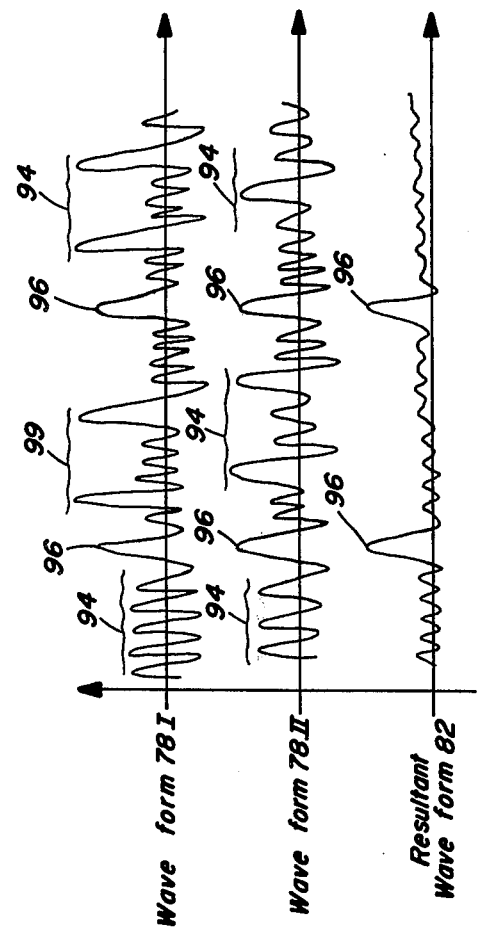
Figure 5:
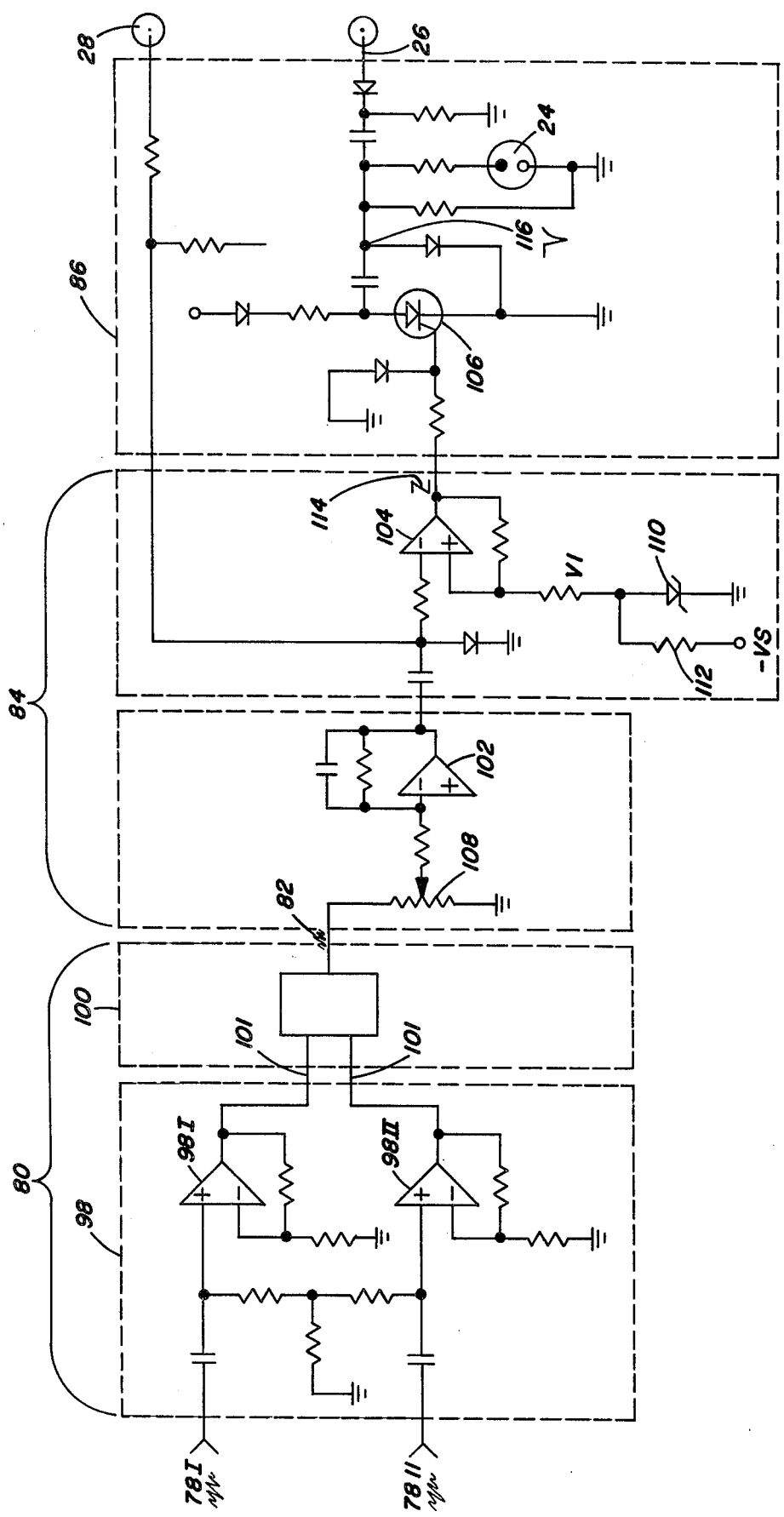

FIG. 4 diagrammatically illustrates waveforms which occur at various times during flaw inspection conducted with a device embodying the present invention; and, FIG. 5 shows in schematic form, post-detection circuitry for use in a system utilizing the present invention.

THE PREFERRED EMBODIMENT

The Overall System

Figure 1:
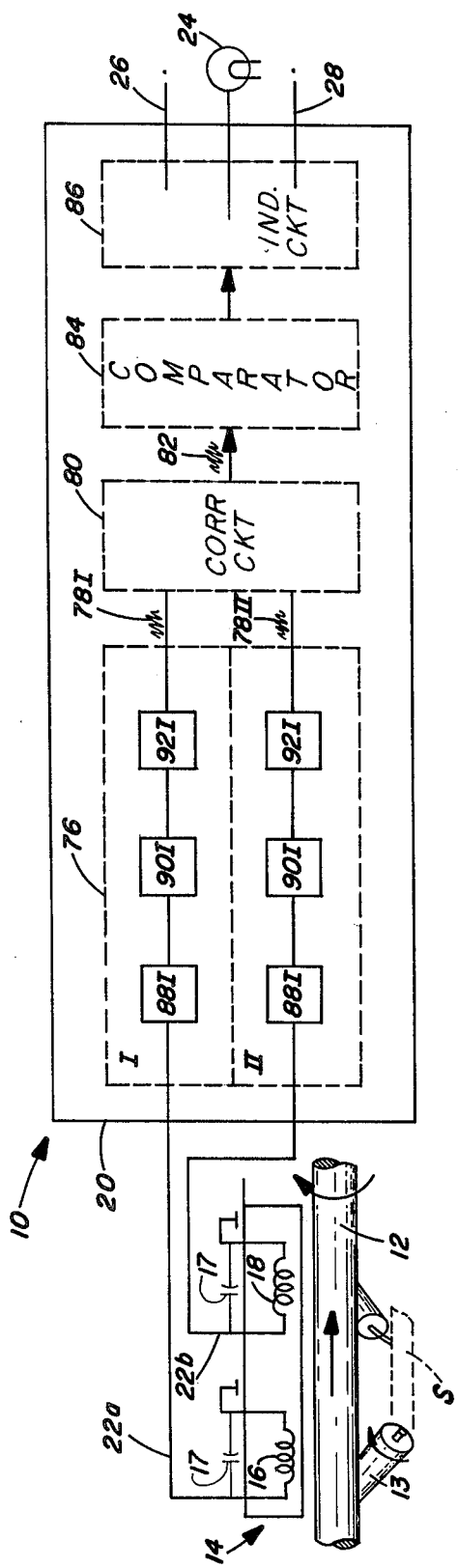
FIG. 1 shows, in block diagram form, an eddy current non-destructive flaw inspection system embodying the present invention.

FIG. 1 illustrates in block diagram form an eddy current flaw detection system 10 for detecting flaws in a steel workpiece 12 in the form of a bar. The system 10 includes a search unit assembly 14 at a workpiece inspection station. The search unit is adapted to be in contact with the surface of the workpiece 12 as the workpiece rotates and moves axially with respect to the search unit. A drive roller, shown diagrammatically at 15, is carried by a workpiece support structure S. The drive roller rotates about an axis whic is canted with respect to the workpiece axis, to drive the workpiece both axially and relatively as indicated by arrows in FIG. 1.

The assembly 14 includes a pair of eddy current detection coils 16, 18 which are electrically coupled to, and energized by, an eddy current test unit 20 via cables 22a, 22b, respectively. The test unit 20 includes a defect lamp 24 for indicating the detected presence of a flaw in the workpiece 12. The test unit 20 has a pair of output terminals 26, 28 respectively adapted to be connected to a flaw marking unit (not shown) and or a recorder (not shown).

The Search Unit 14

Figure 2:
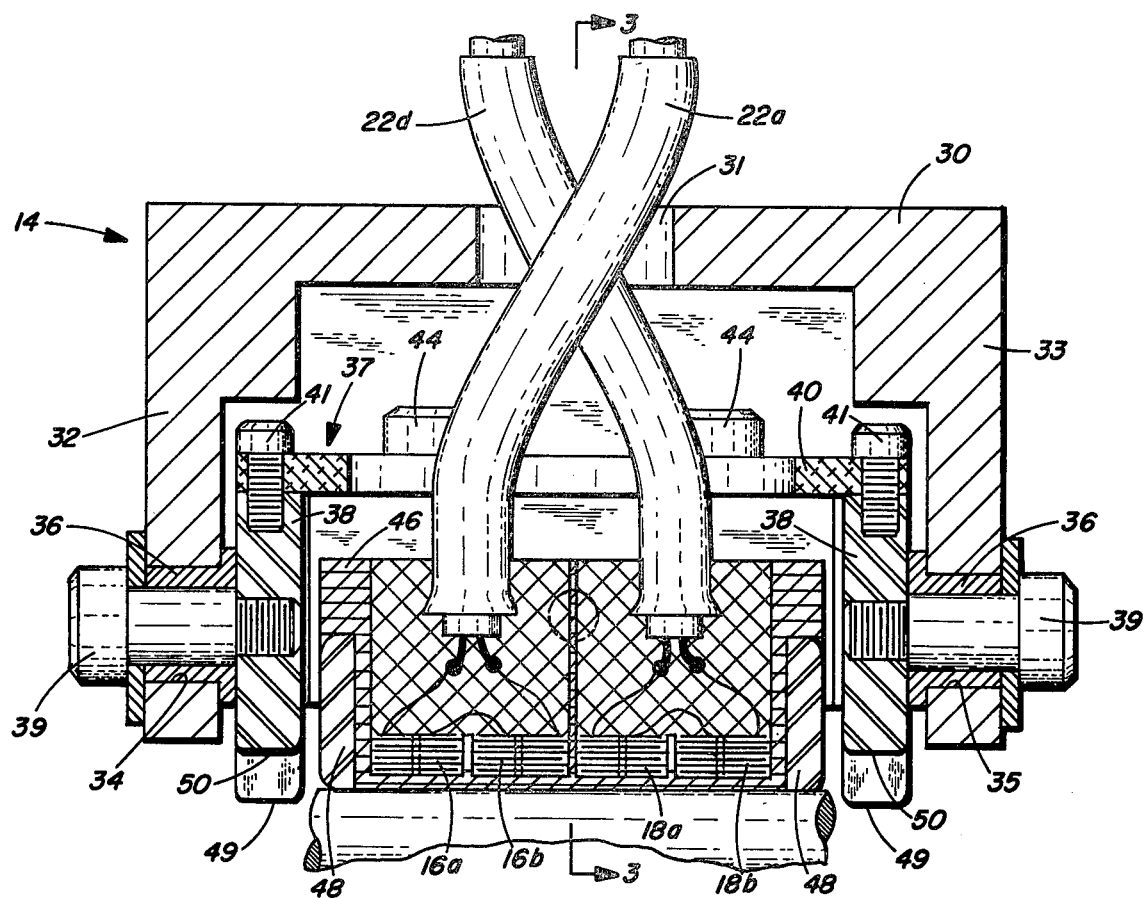
FIG. 2 is a sectional view, as seen from the plane indicated by the line 2—2 of FIG. 3, of a two coil search unit constructed in accordance with the present invention.
Figure 3:
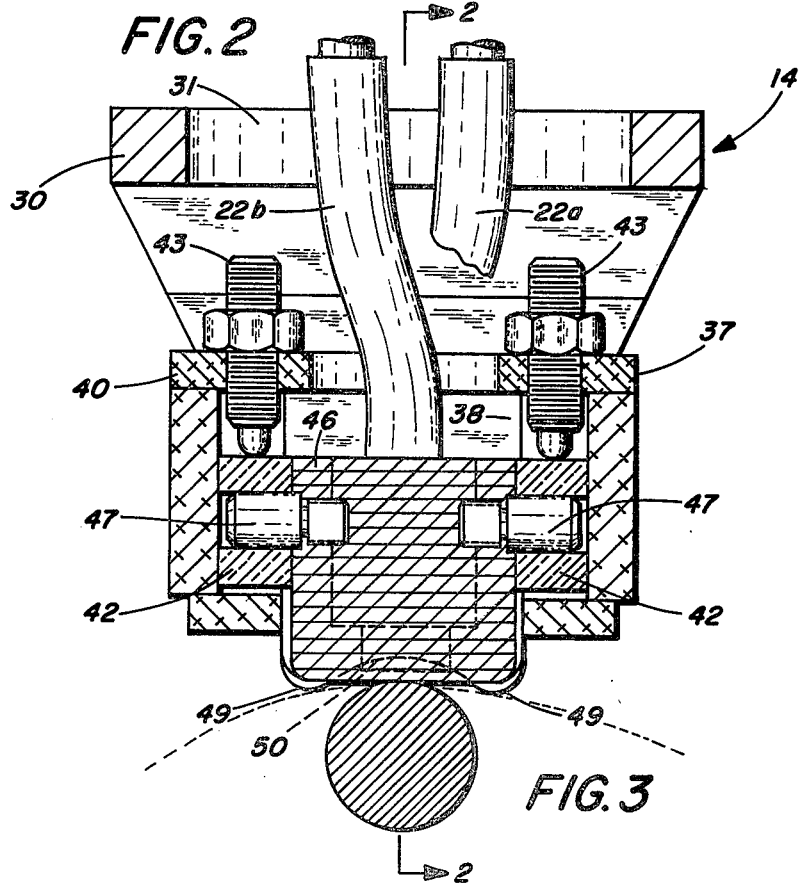
FIG. 3 is a sectional view of the search unit of FIG. 2 as seen from the plane indicated by the line 3—3 of FIG. 2.

Referring to FIGS. 2 and 3 the search unit 14 includes a supporting frame 30. The supporting frame 30 is apertured at 31 to receive the cables 22A, 22B. The supporting frame 30 includes a pair of depending legs 32, 33. The legs 32, 33 have axially aligned apertures 34, 35 each of which carries one of a pair of journaling sleeves 36. An outer gimballing frame 37 is provided. The outer gimballing frame includes a spaced pair of journaling and guide plates 38. A pair of shoulder bolts 39 are provided. The shoulder bolts project through the journaling sleeves 36 and threadedly engage the journaling and guide plates 38 to mount the outer gimballing frame for rotation about the axis of the apertures 34, 35. A top mounting plate 40 is fixed to the journaling and guide plates 38 by bolts 41 to complete the outer gimballing frame 37.

A pair of inner gimbal supports 42 are provided, FIG. 3. These inner gimbal supports are respectively held against a pair of height adjustment screws 43 by bolts 44, two of which are visible in FIG. 2.

A coil support frame 46 is provided. The coil support frame is rotatably carried by the gimbal supports 42 through a pair of shouldered gimballing bolts 47. Thus the coil mounting frame 46 is freely rotatable about the axis of the shoulder bolts 39 and also about the axis of the gimballing bolts 47 so that the coils 16 and 18 can be maintained in appropriate spaced relationship with the workpiece even though the workpiece may have surface irregularities.

A pair of wear shoes 48, are carried by the coil-mounting frame 46, FIG. 2. The wear shoes 48 are axially spaced, relative to a path of workpiece travel, at the ends of the mounting frame 46. Thus, with respect to the workpiece path of travel, the coils 16, 18 are between the spaced wear shoes 48. The journaling and guide plates 38 each have a spaced pair of guide shoulders 49 and a clearance recess 50 between them.

When the search unit 14 is in use, it is biased against a workpiece. The biasing is by known methods such as gravity or spring biasing and the spring may be an air spring in the form of an air cylinder. In its preferred application the search unit 14 is mounted on the apparatus shown and described in U.S. Pat. No. 3,263,809 issued Aug. 2, 1966, which is incorporated by reference.

When the workpiece 12 is of relatively large diameter, as shown in phantom lines in FIG. 3, the guide shoulders 49 ride on the workpiece and maintain appropriate coil-workpiece space relationship. When the workpiece is of somewhat smaller diameter as shown in solid lines in FIG. 3, the workpiece rides against the wear shoes 48 and with the wear shoes being tangential to the workpiece. In this event, the shoulders 49 limit the amount of rocking search unit motion which can occur circumferentially of the workpiece.

The Search Coils 16, 18

As shown in FIGS. 1 and 2, the search unit 14 includes the detection coils 16, 18 which are closely spaced in side-by-side relationship. The detection coils are disposed symmetrically about an imaginary plane which includes the axis of the workpiece and its path of travel. The detection coils are each formed by a pair of coplanar and adjacent windings 16a, 16b and 18a, 18b. Each set of windings is connected in series opposing fashion such that when the system 10 is in use the windings effectively appear as a single search coil. By way of example, each winding is formed of 2350 turns of No. 43 wire wound about a TEFLON bobbin. The search coils 16, 18 are electrically connected to the cables 22a, 22b, respectively.

The coils 16, 18 are energized to produce eddy currents in the workpiece and also sense the presence of flaws. The energizing frequency for a coil is dictated by a resonant frequency of a circuit which includes a coil 16 (for example) and a capacitor 17 connected in parallel with the coil. This resonant frequency is equal to the oscillating or energization frequency at which the workpiece is excited.

The same resonant circuit also senses the induced field produced by eddy currents in the workpiece. The resonant circuit is most sensitive to induced fields that vary at the resonant frequency. Above or below the resonant frequency, the effect of induced fields is sharply alternated. By choosing two coils of different inductances the tuning of the circuits is offset and the effect of mutual coupling between coils is greatly attenuated.

In the present system one coil 16 and capacitor 17 resonates at approximately 27 KHz while the other coil 18 and capacitor 17 resonate at 33 KHz. Different energization frequencies minimize mutual coupling so that there is little or no interaction affect at the two coil outputs. In the preferred embodiment the capacitor 17 is approximately 1000 pf and the coil 16 has an inductance of 20 milliHenries and the second coil 18 has an inductance of 24 milliHenries.

As shown in FIG. 2, each of the search coils 16, 18 is wound relatively flat with the adjacent and oppositely wound windings 16a, 16b, 18a, 18b axially spaced, relative to the workpiece, and uniformly spaced from a workpiece axis. The biasing action of the search unit 14 against the workpiece, maintains the coil sections of the coil windings in uniform spaced relationship with the workpiece. As has been indicated, the workpiece rotates as it is moved axially and the axial and rotational movements are coordinated such that coils 16, 18 each inspect a different spiral path. Ideally these paths are substantially touching, but not overlapping so that an entire workpiece surface is inspected in a minimal amount of time.

The Test Unit 20

The eddy current test unit 20 includes coil energizing and detection circuitry 76 for energizing the search coils 16, 18. The energizing and detection circuitry produces a pair of output waveforms 78. When a flaw has been detected the waveforms 78 have values indicating the presence of the flaw. A signal correlation circuit 80 is provided for receiving the output waveforms 78 and producing a resultant waveform 82. A comparator circuit 84 compares the values of the resultant waveform 82 to a reference voltage VI and produces an output signal when the resultant signal and the reference voltage have a given proportional relationship. Indicating circuitry 86, including the defect lamp 24, produces an output indication of the detected presence of a flaw of at least a predetermined severity.

When a flaw is of sufficient axial length to cause both search coils to produce an output signal, a correlated output signal is produced by the test unit 20. If the flaw is, axially speaking, so short that it causes only one of the coils to produce an output signal, that flaw is considered too small to be of concern and the signal correlation circuitry filters out an output signal from a single one of the coils 16, 18. In short, the signal correlation circuit provides a coincidence function not responding to each coil output signal from one coil which does not coincide with an output signal from the other coil.

To accomplish this signal correlation the coil energizing and detection circuitry 76 includes two channels of eddy current test circuitry, I, II. Each channel I, II is constructed and functions in the manner which is disclosed in detail in U.S. Pat. No. 2,914,726 to William C. Harmon which disclosure is incorporated by reference. For brevity the operation of only channel I, will be described here.

An oscillator 88 energizes the search coil 16 with alternating current of relatively high frequency. This current electromagnetically induces the flow of eddy currents in the workpiece 12. The flow paths of the currents are altered by defects appearing in the surface of the workpiece. The changes in eddy current flow paths produce variations in the amplitude and frequency of the output signal.

A detector circuit 90 senses the oscillator output amplitude variations and produces an output waveform having signals indicating the presence of a flaw. The signal values indicate the severity of the detected flaw, such as its depth. An amplifier 92 conditions the detector circuit output waveform and produces the output waveform 78I which is suitable for interfacing with the signal correlation circuit 80.

As shown in FIG. 4, the waveforms 78I, 78II contain noise signals 94, as well as flaw-stimulated signals 96. The noise 94 is caused by both extrinsic and intrinsic factors, such as unclean or scaly workpieces, and circuit susceptibility to electromagnetic interference. The presence of such noise can mask the presence of a flaw indication reducing the effectiveness of the detection system. With the device and method of the present invention, the noise 94 is filtered out by the signal correlation circuit 80.

As shown in FIG. 5, the signal correlation circuit 80 includes scaling circuits 98 and an analog multiplier 100. Each of the scaling circuits 98 is connected to a respective one of the amplifiers 92 for receiving the waveforms 78. The waveforms 78 are conditioned by the scaling circuits 98 so that they exhibit suitable impedance matching for interfacing with the analog multiplier 100.

The analog multiplier 100 is a commercially available integrated circuit manufactured by Burr-Brown under part number B/B 4206J. This circuit produces an output signal which is a function of the algebraic product of its input signals. By way of example, if we assume the input signals of the analog multiplier to be X(t) and Y(t), and the produced output signal to be Z(t), then $$Z(t) = \frac{X(t) \cdot Y(t)}{10} \tag{1}$$

The above function provides a more simple means of signal correlation than the standard cross-correlation function which states $$Z(t) = \int_{-\infty}^{\infty} X(t) Y(t - T) dt. \tag{2}$$

Expressed another way, the two signals are brought into a time coordinated relationship. When the two signals are multiplied together, noise signals which are random, will be filtered out since zero times anything is zero. On the other hand repetitive flaw signals are multiplied together to produce a resultant amplified flaw signal.

The analog multiplier 100 has a pair of inputs 101, each connected to a respective one of the scaling circuit 98 outputs. The multiplier produces a resultant waveform 82 which is dependent on the amount of similarity of the waveforms 78. As has been stated the search unit assembly 14 is positioned such that flaws in the workpiece 12 are simultaneously detected by both of the search coils 16, 18. Thus, one of the outstanding features of the invention is that the timed coordination of desired signals is achieved by coincident detection and small flaw signals, like noise, are filtered out. In this manner, the time delay T appearing in equation (2) is reduced to zero, simplifying the correlation function and circuitry. The use of the instantaneous product of X(t) and Y(t) in equation (1) also simplifies the circuitry since the integration function required in equation (2) is not required.

The comparator circuit 84 shown in schematic form in FIG. 5 includes a signal conditioning amplifier 102, a source for the reference voltage V1, and a comparator amplifier 104. The resultant signal 82 is received by the signal conditioning amplifier 102 which in cooperation with the potentiometer 108 produces an output signal proportional to the resultant signal. Thus, the conditioning amplifier 102 acts as a gain control circuit for the system 10.

The output of the amplifier 102 is connected to one input of the comparator amplifier 104. The other input of the comparator amplifier receives the reference voltage V1. The reference voltage is formed by the combination of Zener diode 110 and a voltage supply resistor 112 connected to the power supply-Vs. The comparator amplifier 104 compares the output signal value of the conditioning amplifier 102 to the reference voltage V1 and produces an output signal when the output signal value exceeds the reference voltage V1. This causes the output of the comparator amplifier 104 to produce a waveform 114 having a negative going transition.

The reference voltage V1 is selected for the minimum depth of the flaw to be detected. As stated previously, the resultant signal 82 has a value indicating the depth of a detected flaw. The value of the reference voltage V1 can be chosen and adjusted by selecting a Zener diode 110 having the desired Zener voltage. By way of example, as shown in FIG. 4, the Zener diode 110 is a commercially available diode having a 3.9 v Zener voltage, which can be purchased from Texas Instruments, Inc., under part number IN746.

The output of the comparator amplifier 104 is connected to the indicating circuitry 86 and controls the gate electrode of a silicon controlled rectifier (SCR) 106. When the output of the conditioning amplifier 104 exceeds the value of the reference voltage V1, the negative going waveform 114 is produced at the output of the comparator amplifier 104 to activate the SCR 106. The conduction of the SCR 106 produces a negative going pulse, having a short duration, at a node 116.

The indicating circuitry 86 includes the defect lamp 24, which in response to the negative going pulse produced at node 116, flashes to indicate the detected presence of a flaw in the workpiece 12. The indicating circuitry also contains the output terminal 26 which is suitable for connection to a suitable flaw marking device.

The output of the amplifier 102 is a.c. coupled to an output terminal 28 suitable for connection to a recorder for recording a permanent record of the position and severity of the flaw.

While a preferred embodiment of the present invention has been illustrated and described, the invention is not limited to the construction shown. Various adaptations, modifications and uses of the invention are intended to and do fall within the spirit and the scope of the attendant claims.

What is claimed is:

1. An eddy current flaw inspection system comprising:
   (a) a supporting structure;
   (b) a detection unit carried by the supporting structure and positioned at a workpiece inspection station;
   (c) the structure including means to spirally drive a cylindrically contoured workpiece along a workpiece path of travel extending through the inspection station;
   (d) a pair of side-by-side weakly coupled detection coils positioned symmetrically about a plane transverse to the axis of the path of travel for concurrent inspection of a pair of axially spaced portions of a workpiece;
   (e) the detection unit including gimballing structure supporting the coils for movement relative to a workpiece whereby the coils can be maintained in substantially constant spaced relationship with the workpiece irrespective of irregularities in a workpiece surface;
   (f) each of the coils including oppositely wound portions to inhibit emission of signals by the coils other than those induced by detected flaws;
   (g) a pair of coil signal drive and detection circuits each connected to a different one of the coils for driving the coils at resonant frequencies differing one from another by less than a ratio of about 1.5:1 and for receiving and processing flaw indicating signals from the connected coils;
   (h) a correlation circuit connecting to the processing circuits for emitting a resultant algebraic product signal whenever flaw indication signals are concurrently emitted by the two detection coils; and,
   (i) a flaw signal indicator connected to the correlation circuit for actuation by such resultant signals.

2. In an eddy current flaw inspection system for detecting workpiece surface flaws and the like including circuitry for inducing eddy current flow in a workpiece, the improvement comprising:

(a) a pair of substantially coplanar detection coils spaced along the workpiece for detecting flaw indicative variations in eddy current flow in a workpiece and adapted to produce flaw indicative output signals; and
(b) a coincidence circuit connected to the detection coils for rejecting a flaw indicative signal from one coil unless it is coincident with a signal from the other coil;
(c) the eddy current producing circuits characterized by different but similar resonant energization frequencies differing one from another by less than a ratio of about 1.5:1 to reduce inductive cross talk between detection coils.

3. A method of eddy current flaw inspection comprising:
(a) positioning a detector unit including a pair of weakly coupled detector coils along a path of travel with each coil comprising a circuit having a different but similar resonant frequency with respect to the other circuit said resonant frequencies differing one from another by less than a ratio of about 1.5:1;
(b) relatively moving a workpiece and the detector unit along the path of travel while maintaining the detector unit in flaw-sensing relationship with the workpiece;
(c) inducing a flow of eddy currents in the workpiece by energizing the circuits with their respective resonant frequencies;
(d) sensing flaw indication variations in eddy current flow with the coils; and
(e) producing a resultant output signal whenever concurrent flaw indication signals are received from the coils indicative of concurrent detection of a given flaw.

4. The method of claim 3 further indicating the step of rejecting an output signal from one detection coil unless it is coincident with a signal from the other coil.

5. A system for detecting flaws in a metallic workpiece employing the generation of eddy currents within the workpiece, said system comprising:
(a) two detection circuits each including a detection coil positionable proximate a path along which a metallic workpiece may be relatively moved;
(b) a first drive circuit coupled to a first of the detection circuits for energizing the coil of said first detection circuit at a frequency for inducing eddy currents predominantly penetrating to a predetermined depth within the workpiece;
(c) a second drive circuit coupled to the other detection circuit for energizing the coil of such other circuit at a frequency different from said first frequency, said different frequency being selected for inducing eddy currents penetrating within the workpiece predominantly to the same depth as that to which the first detection circuit induces eddy currents, and
(d) a sensing circuit coupled to the detection circuits and responsive to variations in eddy current flow sensed by the detection coils to produce a flaw indication signal.

6. An eddy current system for detecting flaws in an elongated metallic workpiece movable along a longitudinal path, said system comprising:
(a) a first detection circuit having a first resonant frequency and comprising a first detection coil;
(b) a second detection circuit having a second resonant frequency different from said first resonant frequency in a ratio of less than approximately 1.5 to 1 and comprising a second detection coil;
(c) means for supporting said first and second detection coils in a weakly coupled side-by-side relationship with their axes being approximately perpendicular to the workpiece path;
(d) a first drive circuit for energizing said first detection circuit at a frequency approximately equal to said first resonant frequency;
(e) a second drive circuit coupled to said second detection circuit for energizing said second detection circuit at a frequency approximately equal to said second resonant frequency;
(f) a first sensing circuit coupled to the first detection circuit for sensing variations in eddy currents caused by energization of said first detection coil;
(g) a second sensing circuit coupled to said second detection circuit for sensing variations in eddy currents within the workpiece caused by energization of said second detection coil;
(h) a circuit responsive to said first and second sensing circuits to produce a signal representing a product of said outputs, and
(i) a comparator circuit for producing an indication when said product exceeds a predetermined value.

* * * * *